(12) United States Patent
Pascolo

(10) Patent No.: US 10,646,576 B2
(45) Date of Patent: May 12, 2020

(54) IMMUNOSTIMULATING-TOXIC RNA IN ALKALINE EARTH METAL FORMULATION

(71) Applicant: spRNA GmbH, Zurich (CH)

(72) Inventor: Steve Pascolo, Zurich (CH)

(73) Assignee: spRNA GmbH (CH)

( * ) Notice: Subject to any disclaimer, the term of this patent is extended or adjusted under 35 U.S.C. 154(b) by 0 days.

(21) Appl. No.: 15/770,092

(22) PCT Filed: Oct. 12, 2016

(86) PCT No.: PCT/EP2016/075455
§ 371 (c)(1),
(2) Date: Apr. 20, 2018

(87) PCT Pub. No.: WO2017/068156
PCT Pub. Date: Apr. 27, 2017

(65) Prior Publication Data
US 2018/0311366 A1    Nov. 1, 2018

(30) Foreign Application Priority Data

Oct. 21, 2015 (EP) ..................................... 15190920

(51) Int. Cl.
| | | |
|---|---|---|
| *C12N 15/117* | (2010.01) | |
| *A61K 31/713* | (2006.01) | |
| *A61K 31/7115* | (2006.01) | |
| *A61K 31/712* | (2006.01) | |
| *A61K 47/02* | (2006.01) | |
| *A61K 47/55* | (2017.01) | |
| *A61K 47/54* | (2017.01) | |
| *A61K 9/08* | (2006.01) | |
| *A61K 47/12* | (2006.01) | |

(52) U.S. Cl.
CPC ................ *A61K 47/55* (2017.08); *A61K 9/08* (2013.01); *A61K 31/712* (2013.01); *A61K 31/7115* (2013.01); *A61K 47/02* (2013.01); *A61K 47/12* (2013.01); *A61K 47/549* (2017.08); *C12N 15/117* (2013.01); *C12N 2310/17* (2013.01); *C12N 2310/351* (2013.01); *C12N 2320/31* (2013.01)

(58) Field of Classification Search
None
See application file for complete search history.

(56) References Cited

U.S. PATENT DOCUMENTS 9,226,959 B2 * 1/2016 Kramps ................. A61K 39/39

FOREIGN PATENT DOCUMENTS

WO    2012103985 A2    8/2012

OTHER PUBLICATIONS

Benteyn, Daphne et al. "mRNA-based dendritic cell vaccines.",Expert Review of Vaccines, vol. 14, No. 2, Sep. 8, 2014 (Sep. 8, 2014), pp. 1-16.
Bringmann, Anita et al. "RNA Vaccines in Cancer Treatment.", Journal of Biomedicine & Biotechnology, 623687, 2010, pp. 1-12 XP002765542, ISSN: 1110-7243, DOI: 10.1155/2010/623687.
Jinming, Li et al. "Messenger RNA vaccine based on recombinant MS2 virus-like particles against prostate cancer." International Journal of Cancer, vol. 134, No. 7, Apr. 1, 2014 (Apr. 1, 2014) , pp. 1683-1694 XP002765541, ISSN: 1097-0215, DOI: 10.1002/ijc. 28482, p. 1693.

* cited by examiner

*Primary Examiner* — Tracy Vivlemore
(74) *Attorney, Agent, or Firm* — St Onge Steward Johnston & Reens LLC

(57) ABSTRACT

A composition including an immunostimulating RNA molecule in a dication containing solution wherein the RNA includes a chemical modification which is toxic to cancer or tumor cells. Pharmaceutical compositions incorporate the immunostimulating RNA with tumor cytotoxicity. Methods for treating cancer and tumors use the solution of the immunostimulating RNA with tumor cytotoxicity.

26 Claims, No Drawings
Specification includes a Sequence Listing.

IMMUNOSTIMULATING-TOXIC RNA IN ALKALINE EARTH METAL FORMULATION

FIELD OF THE INVENTION

The present invention relates to a composition comprising an RNA molecule in a dication containing solution wherein the RNA comprises a chemical modification being toxic for tumor cells and has an immunostimulating activity. The present invention further relates to corresponding pharmaceutical compositions as well as methods for treating cancer and tumors using the inventive RNA complexes.

SEQUENCE LISTING

This application was filed with and incorporates by reference a Sequence Listing having the file name 1AB4490.txt, which was created on Apr. 20, 2018 having a file size of 4.80 KB. This Sequence Listing contains the same matter as the Sequence Listing filed with PCT Application No. PCT/EP2016/07545. This application includes and hereby incorporates by reference a corrected Sequence Listing having the file name S0405WO_ST25_corr.txt, which was created on May 30, 2018 and is 4.81 KB.

BACKGROUND OF THE INVENTION

WO-A-2012/103985, which is hereby incorporated by reference, discloses cell penetrating RNA formulations consisting of RNA molecules having an alkali metal as counter ion and being formulated in the presence of dications. These RNA formulations are disclosed to be useful in stimulating Toll-like receptors (TLRs) and other intracellular sensors of immunity (such as RIG-I) resulting in triggering of immune modulation.

The technical problem underlying the present invention is to provide improved RNA molecules useful in the treatment of tumors and cancer.

SUMMARY OF THE INVENTION

The solution to the above technical problem is provided by the embodiments of the present invention as described herein and in the claims.

According to a first aspect, the present invention provides a composition comprising an RNA molecule in a dication containing solution wherein the RNA comprises a chemical modification being cyotoxic, in particular toxic for tumor and cancer, respectively, cells and has an immunostimulating activity. More specifically, for providing the RNA molecule with an immunomodulating, in particular immunostimulating activity, it comprises at least a structure activating at least one pattern recognition receptor (PRP). According to preferred embodiments, the RNA molecule of the invention comprises a structure activating a Toll-like receptor (TLR), more preferably TLR-3, TLR-7 and/or TLR-8 and/or a RIG-I-like receptor (RLR), more preferably RIG-I and/or MDA-5.

The invention further includes methods of making the modified cytotoxic to tumors immunostimulating RNA of the invention.

The present invention further provides pharmaceutical compositions in the form of an injectible formulation comprising the modified cytotoxic to tumors immunostimulating RNA of the invention in combination with a pharmaceutically acceptable excipient such as Ringer Lactate.

The present invention further provides methods of use of penetrating RNA formulation as defined herein for the preparation of a pharmaceutical composition or medicament for immunomodulation and cancer or tumor, respectively, therapy in a subject, preferably a mammal, especially a human The present invention further provides methods of concurrent stimulation of a host immune response and cytotoxic treatment directed at cancer cells and tumor cells. The methods provide for treating cancer and/or tumor in a subject, in particular by stimulating a host immune response and introducing an anti-metabolite into cancer/tumor cells in a subject, preferably a mammal, especially a human.

DETAILED DESCRIPTION OF THE INVENTION

RNA molecules that may be contained in the compositions of the invention for activating TLR-3 are typically double-stranded and comprise at least 45 bp (or at least contain a double-stranded section of at least that length).

RNA molecules which may be included in the compositions of the invention triggering TLR-7 and/or -8 are typically single-stranded.

RNA molecules of use in the compositions of the invention triggering RIG-I and/or MDA-5 comprise a free triphosphate group at a 5' end of the molecule. Preferably, the free 5'-triphosphate is attached to a blunt end dsRNA, wherein the dsRNA may be blunt at one or both ends, In the latter case the dsRNA can have a free triphosphate group at the 5' terminus of one strand or at both 5' termini.

According to the invention, the RNA molecule may trigger one or more kinds of PRPs, e.g. in one embodiment, the RNA molecule can trigger TLR-3 and RIG-I.

According to a second aspect, the RNA molecule is complexed with alkaline earth metal ions such as calcium.

In certain embodiments of the invention, the RNA contained in the composition is preferably present in a complex with alkali metal ions, more preferably $Na^+$.

According to further preferred embodiments, the RNA molecule contains a sequence of at least four consecutive, most preferred six consecutive G residues and/or a sequence of at least five consecutive U residues and/or the sequence motif $GPu_nG$ (with Pu being G or A and n being an integer of from 1 to 4 or more) and/or the sequence motif $GGA_mAGG$ (with m being an integer of from 0 to 4 or more).

The presence of at least four consecutive G residues, most preferred six G residues in the RNA of the invention provides for a cell penetrating activity, as has been described previously in WO-A-2012/103985.

According to the present invention, the letter "G" means guanosine (guanine associated to a ribose). According to the present invention, the letter "U" means uridine (uracil associated to a ribose). According to the present invention, the letter "A" means adenosine (adenine associated to a ribose). According to the present invention, the letter "C" means cytidine (cytosine associated to a ribose).

Besides the above preferred sequence requirements (wherein the RNA molecule can comprise one or more of the sequence features as described herein), the sequence of the RNA molecule is not restricted. Preferred RNA molecules of the invention, however, contain more than 20% U residues, more preferred at least 25% U residues.

As used herein, the term "U content" refers to the amount of nucleosides of a particular RNA molecule or RNA sequence (including mtiRNA) that are uridine (U) typically expressed as a percent. Where the sequence of particular RNA is known, the U content can be determined using the formula:

$$\frac{U}{A+U+G+C} \times 100 \qquad \text{(Formula I)}$$

wherein G, C, A and U refer to the number of each residue in the particular RNA molecule or RNA sequence, to provide a percent U content.

As explained herein, all or a portion such as at least 5%, at least 10%, at least 20%, at least 30%, at least 40%, at least 50%, at least 60%, at least 70%, at least 80%, at least 90%, at least 95%, or at least 98% of the U residues of a mtiRNA may be modified so as to provide the cytotoxic nucleotide or cytotoxic nucleotide analog, for example fluorouridine.

In one embodiment the RNA molecule contained in the composition of the present invention is preferably a RNA oligonucleotide prepared through chemical synthesis, more preferably having a length of from 6 to 100 nucleotides. In other embodiments, the RNA molecule can be made enzymatically, preferably through in vitro transcription, and typically comprises more than 100 nucleotides such as from 100 to 10,000 nucleotides. As used herein, the term "oligo (ribo)nucleotide" shall mean multiple ribonucleotides, i.e. a molecule comprising a ribose) linked to a phosphate group and to an organic base selected from the group consisting of cytosine (C), uracil (U) adenine (A) and guanine (G). An oligomer generally is defined to consist of a finite number of monomer units, which number typically ranges from a few to more than a hundred. In the context of the present invention, an oligoribonucleotide has a length of from about 6 to about 100 ribonucleotides. More preferred oligoribonucleotide have length of from 12 to 40 nt, and even more preferably the length is from 16 to 24 nt. The same length considerations (in base pairs, bp) are valid for double stranded species.

The second activity of the inventive RNA molecule, namely a tumor cytotoxic activity, is provided by a suitable chemical modification, i.e. the RNA molecule comprises at least one cytotoxic nucleotide and/or at least one cytotoxic chemical moiety linked to the RNA.

Examples of cytotoxic chemical moieties linked to the inventive RNA comprise small toxic chemical groups such as a cyanide group and, according to certain preferred embodiments of the invention, tumor toxins such as tyrosine kinase inhibitors (e.g. Sunitinib or Sorafenib) or inhibitors of mutated oncogens (e.g. Vemurafenib).

Tumor cytotoxic nucleotides incorporated into the RNA molecule are preferably cytotoxic nucleotide analogues comprising a chemical modification on the base and/or sugar moiety.

Particularly preferred examples of cytotoxic nucleotides having a chemical modification at the base moiety include 5-fluoro-uridine (5-FU), 6-mercaptopurine, pentostatin and 2-chloro-adenine. Especially preferred cytotoxic nucleotides containing a chemical modification at the sugar moiety include nucleotides based on cytarabine, fludarabine or gemcitabine.

The term "cytotoxic nucleotide or cytotoxic nucleotide analog" as used herein refers to any nucleotide or nucleotide analog, in particular nucleotide or nucleotide analog which can be incorporated into nucleic acids such as RNA, which is cytotoxic or comprises a moiety such as a nucleoside or nucleoside analog or nucleobase or nucleobase analog which is cytotoxic. The cytotoxic nucleotide or cytotoxic nucleotide analog may be cytotoxic if part of a nucleic acid molecule, in particular RNA molecule, and/or following release of a cytotoxic moiety such as a nucleoside or nucleoside analog or nucleobase or nucleobase analog. Typically, analogs are similar to natural compounds and moieties, however, they are modified so as to provide certain effects such as cytotoxicity. Accordingly the term "cytotoxic nucleotide or cytotoxic nucleotide analog" includes cytotoxic purine nucleoside analogs and cytotoxic pyrimidine nucleoside analogs such as cytotoxic analogs or homologs of A, G, U, C, dA, dG, dT, dC.

In various embodiments, the modifications of a cytotoxic nucleotide or cytotoxic nucleotide analog to provide cytotoxicity are on the base moiety (e.g. 5-fluoro-uridine (5-FU), 6-mercaptopurine, deoxycoformycin (Pentostatin) and 2-chloro-adenine) or on the sugar moiety (e.g. cytosine arabinoside (cytarabine) or Gemcitabine) or both (e.g. Fludarabine).

In various embodiments, adenine and/or guanine residues are modified in 6-mercaptopurine or deoxycoformycin or fludarabine, adenine residues are modified in 2-chloro-adenine, cytidine residues are modified in cytarabine or gemcitabine and/or uracil residues are modified in fluorouracil such as 5-fluorouracil. In one particularly preferred embodiment, uracil residues are modified in fluorouracil such as 5-fluorouracil.

According to the invention, the term "cytotoxic nucleotide or cytotoxic nucleotide analog" includes, but is not limited to, nucleotide and nucleotide analogs comprising a moiety selected from the group consisting of:

Azacitidine (4-Amino-1-β-D-ribofuranosyl-1,3,5-triazin-2 (1H)-one),

Cladribine (5-(6-Amino-2-chloro-purin-9-yl)-2-(hydroxymethyl)oxolan-3-ol),

Clofarabine (5-(6-amino-2-chloro-purin-9-yl)-4-fluoro-2-(hydroxymethyl)oxolan-3-ol), Cytarabine (4-amino-1-[(2R,3S,4R,5R)-3,4-dihydroxy-5-(hydroxymethyl)oxolan-2-yl] pyrimidin-2-one), Decitabine (4-Amino-1-(2-deoxy-β-D-erythro-pentofuranosyl)-1,3,5-triazin-2(1H)-one), Floxuridine (5-Fluoro-1-[4-hydroxy-5-(hydroxymethyl)tetrahydrofuran-2-yl]-1H-pyrimidine-2,4-dione), Fludarabine ([2R,3R,4S,5R)-5-(6-amino-2-fluoro-purin-9-yl)-3,4-dihydroxy-oxolan-2-yl]methoxyphosphonic acid), Fluorouridine such as 5-fluoro-uridine, Gemcitabine (4-amino-1-(2-deoxy-2,2-difluoro-β-D-erythro-pentofuranosyl)pyrimidin-2(1H)-on), Nelarabine ((2R,3S,4S,5R)-2-(2-amino-6-methoxy-purin-9-yl)-5-(hydroxymethyl)oxolane-3,4-diol), Pentostatin ((R)-3-((2R,4S,5R)-4-hydroxy-5-(hydroxymethyl)tetrahydrofuran-2-yl)-3,6,7,8-tetrahydroimidazo[4,5-d][1,3]diazepin-8-ol), Azathioprine (6-[(1-Methyl-4-nitro-1H-imidazol-5-yl)sulfanyl]-7H-purine), Carmofur (5-fluoro-N-hexyl-2,4-dioxo-pyrimidine-1-carboxamide), Mercaptopurine (3,7-dihydropurine-6-thione), Tegafur ((RS)-5-Fluoro-1-(tetrahydrofuran-2-yl)pyrimidine-2,4(1H,3H)-dione), and Tioguanine (2-amino-1H-purine-6(7H)-thione).

Useful classes of cytotoxic agents (cytotoxins) include, for example, antitubulin agents, DNA minor groove binders (e.g., enediynes and lexitropsins), DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, nitrosoureas, platinols, pre-forming compounds, purine antimetabolites, puromycins, radiation sensitizers, steroids, taxanes (e.g., paclitaxel and docetaxel), topoisomerase inhibitors, vinca alkaloids, or the like.

Individual cytotoxic agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluordeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide, 6-thioguanine, thioTEPA, topotecan, vinblastine, vincristine, vinorelbine, VP-16 and VM-26.

Examples of anti-tubulin agents include, but are not limited to, dolastatins (e.g., auristatin E, AFP, MMAF, MMAE, AEB, AEVB), maytansinoids, taxanes (e.g., paclitaxel, docetaxel), T67 (Tularik), vinca alkyloids (e.g., vincristine, vinblastine, vindesine, and vinorelbine), baccatin derivatives, taxane analogs (e.g., epothilone A and B), nocodazole, colchicine and colcimid, estramustine, cryptophysins, cemadotin, combretastatins, discodermolide, and eleutherobin.

In one embodiment, the term "cytotoxin" refers to cytotoxic antibodies. The term "cytotoxic antibody" includes but is not limited to monoclonal antibodies (mABs) having the ability to target diseased cells such as tumor cells, marking them for immune-effector mediated cell killing (complement-dependent cytotoxicity (CDC), antibody-dependent cellular cytotoxicity (ADCC)) and/or leading to reduced proliferation and apoptosis.

The term "cytotoxin" also includes antigen-specific structures such as mABs conjugated to cytotoxic drugs as described herein. By combining the unique targeting capabilities of an antibody with the cancer-killing ability of a cytotoxic drug, antibody-drug conjugates (ADCs) exhibit lower side effects and provide a wider therapeutic window compared to traditional chemotherapeutic agents. In one preferred embodiment, the target antigen (disease-associated antigen) bound by the cytotoxic antibody is localized on the cell surface and accessible to circulating antibody.

According to the invention, the term "antigen-specific structure" includes any compound that has a binding capacity to a target antigen such as a disease-associated antigen. The term includes molecules such as antibodies and antibody fragments, bispecific or multispecific molecules, chimeric antigen receptors (CARs) and all artificial binding molecules (scaffolds) having a binding capacity to the target including but not limited to nanobodies, affibodies, anticalins, DARPins, monobodies, avimers, and microbodies. In one embodiment said binding is a specific binding.

The term "antibody" refers to a glycoprotein comprising at least two heavy (H) chains and two light (L) chains inter-connected by disulfide bonds. The term "antibody" includes monoclonal antibodies, recombinant antibodies, human antibodies, humanized antibodies and chimeric antibodies. Each heavy chain is comprised of a heavy chain variable region (VH) and a heavy chain constant region. Each light chain is comprised of a light chain variable region (VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "RNA covalently attached to a cytotoxin" includes situations where one or more molecules of the same cytotoxin are covalently attached to an RNA molecule as well as where different cytotoxins are covalently attached to an RNA molecule. In the latter situation, one or more molecules of each of the different cytotoxins may be attached to an RNA molecule, or a combination thereof (e.g. one molecule of one cytotoxin is attached while several molecules of another cytotoxin are attached).

The generation of RNA-cytotoxin conjugates can be accomplished by any technique known to the skilled artisan. RNA-cytotoxin conjugates can be prepared by binding the cytotoxin to RNA in accordance with a conventional technique. RNA and a cytotoxin may be directly bound to each other via their own linker groups or indirectly via a linker or other substance. There are many linking groups known in the art for making RNA-cytotoxin conjugates. A linker preferably comprises one or more functional groups that react with either or both of the RNA and the cytotoxin.

In especially preferred embodiments, the RNA molecule contained in the compositions according to the invention is selected from the following (or comprises the following) sequences:

```
                                              (SEQ ID NO: 1)
5'-A5A 55C 55G 5A5 GGG GGG-3'

(SEQ ID NO: 2)
5'-GGG GGG A55 C55 G5A 5A5-3'

(SEQ ID NO: 3)
5'-AG5 G55 A5C 55G 5A5 GGG GGG-3'

(SEQ ID NO: 4)
5'-A5A 55C 55G 5A5 GGG GGG GGG GGG-3'

(SEQ ID NO: 5)
5'-GGG GGG A5A 55C 55G 5A5 GGG GGG-3'

(SEQ ID NO: 6)
5'-A5A 555 55G 5A5 GGG GGG-3'

(SEQ ID NO: 7)
5'-GGG GGG A5A 55C 55G 5A5 GGG GGG-3'
``` wherein "5" denotes a 5-fluoro-uridine (=5FU) nucleotide, and the other nucleotide abbreviations are defined as outlined above.

According to preferred embodiments, the RNA molecule of the present invention can comprise, optionally besides the one or more tumor cytotoxic nucleotide analogues, other chemically modified or labelled, respectively, nucleotide analogues known in the art. According to preferred embodiments, the inventive RNA is preferably single-stranded and, besides the tumor cytotoxic modification, usually does not contain (further) chemical modifications to its subunits (e.g. on the base, or on the phosphate, or on the ribose residue). However, modifications (e.g. phosphorothioate backbone, peptide nucleic acid: PNA, backbone, 2' Fluoro) that could help manufacturing or formulation or biological activities or linkage to a cargo of the RNA described herein are also subject of the present invention. The 5' end of the RNA can be OH, monophosphate or triphosphate, the latter, as mentioned before, allowing stimulation of the cytosolic RIG-I, thus enhancing immunostimulation.

According to particularly preferred embodiments of the invention, the RNA molecule contains (i) at least four consecutive G residues, (ii) at least one tumor cytotoxic chemical modification as outlined above, and (iii) an immunostimulating structure or component, respectively, such as one ore several G and/or U residues being immunostimulating through TLRs and/or a free 5' triphosphate group as a ligand of cytosolic RLRs such as RIG-I.

In an embodiment of the invention, the RNA molecule is present in complex with alkali metal ions, i.e. lithium, sodium, potassium, rubidium, caesium and/or francium ions, preferably sodium ($Na^+$) or potassium ($K^+$). Most preferred, the complex contains the RNA molecule and sodium ions. Complexes of the invention may be prepared by precipitating the RNA molecule using an alkali metal salt such as sodium chloride (NaCl) and/or sodium acetate (NaAc) and an alcohol, preferably ethanol or propanol. According to an alternative embodiment, the alkali metal-RNA complex may be prepared by ion exchange chromatography, preferably using commercially available HPLC systems. With respect to further details for the preparation protocol, it is referred to WO-A-2012/003985.

The present invention relates to formulations containing the RNA molecule as defined herein, preferably RNA-alkali metal complexes, more preferably RNA-sodium-complexes in a dication-containing solution, preferably an aqueous solution. Dications for use in this aspect of the invention are preferentially selected from alkaline earth metals, i.e. beryllium, magnesium, calcium, strontium, barium and/or radium, and transition metals such as manganese and/or cobalt. Especially preferred solutions of the inventive formulation contain calcium ($Ca^{2+}$), magnesium ($Mg^{2+}$) and/or manganese ($Mn^{2+}$), with calcium being the most preferred dication species. The dication, in particular $Ca^{2+}$, is preferably used at a concentration of 0.2 mM to 20 mM. Particularly preferred solutions for providing the inventive RNA formulation are Ringer solutions such as Ringer, Ringer lactate or Ringer acetate. Especially preferred formulations of the invention are prepared by providing an RNA as defined above (preferably containing a poly-G sequence, a poly-U sequence and/or the sequence motif $GPu_nG$ and/or the sequence motif $GGA_mAGG$ as defined above) or a corresponding RNA-alkali metal complex at a concentration of between 0.1 mg/ml to 3 mg/ml in Ringer lactate or another $Ca^{2+}$-containing solution. More preferred formulations of the invention contain RNA-sodium complexes prepared by diluting an RNA-sodium complex as described herein to a concentration of between 0.1 mg/ml to 3 mg/ml in Ringer lactate or another $Ca^{2+}$-containing solution. As a practical example, the dried RNA or RNA-alkali metal complex (typically being present in lyophilized form) may be suspended in Ringer lactate or other suitable $Ca^{2+}$-containing solution so that the appropriate concentration of the RNA or RNA-alkali metal complex, respectively, is attained.

The present invention is also directed to pharmaceutical compositions containing the RNA molecule of the invention or their complexes or formulations as described herein, optionally in combination with one or more pharmaceutically acceptable carrier(s), excipient(s) and/or diluent(s).

In the inventive compositions (RNA formulation and/or pharmaceutical composition), one or several RNA sequences such as oligonucleotide sequences can be combined to generate the final composition. Attachment of the RNA(s) to a cargo (e.g. a peptide) can be used so that the formulated RNA introduces relevant, in particular bioactive, moieties into cells. It is also contemplated that RNA compositions of the invention comprise one RNA species having an immunostimulating activity (as outlined before) and another RNA contains the one or more chemical modifications (as defined above) providing the tumor toxicity.

To further increase effectiveness, the immunostimulating compositions according to the invention can comprise one or more adjuvants, preferably to achieve a synergistic effect of immunostimulation. "Adjuvant" in this context encompasses any compound which promotes an immune response. Various mechanisms are possible in this respect, depending on the various types of adjuvants. For example, compounds which allow the maturation of dendritic cells (DCs), e.g. lipopolysaccharides or CD40 ligand, form a first class of suitable adjuvants. Generally, any agent which influences the immune system of the type of a "danger signal" (LPS, gp96, dsRNA etc.) or cytokines, such as GM-CSF, can be used as an adjuvant which enables an immune response to be intensified and/or influenced in a controlled manner. CpG oligodeoxynucleotides can optionally also be used in this context, although their side effects which occur under certain circumstances are to be considered. Because of the presence of the immunostimulating/tumor cytotoxic agent according to the invention comprising RNA as the primary immunostimulant, however, only a relatively small amount of CpG DNA is necessary (compared with immunostimulation with only CpG DNA). Particularly preferred adjuvants are cytokines, such as monokines, lymphokines, interleukins or chemokines, e.g. IL-1, IL-2, IL-3, IL-4, IL-5, IL-6, IL-7, IL-8, IL-9, IL-10, IL-12, INFα, INF-γ, GM-CFS, LT-α, or growth factors, e.g. hGH. Further known adjuvants are aluminium hydroxide, Freund's adjuvant or oil such as Montanide®, most preferred Montanide® ISA51. Lipopeptides, such as Pam3Cys, are also particularly suitable for use as further adjuvants in the compositions of the present invention.

In a preferred embodiment, the RNA compositions according to the invention can also be used in conjunction with another therapeutic reagent. The RNA composition of the present invention may on its own synergize with other treatments such as chemotherapeutic drugs for cancer patients.

Many chemotherapy regimens (e.g. etopophos, cis-platin, carbo-platin, etc.) or radiotherapy protocols can be used at dosages that do not severely affect the immune system. Thus, during radio/chemotherapy in cancer patients, the RNA compositions of the invention can be used whereby the death of tumor cells can be accompanied by the enhanced induction of an immune response. Systemic, preferably intra-venous and/or sub-cutaneous, as well as local, preferably intra-tumor or intradermal, injections of an RNA composition according to the present invention in patients under radio/chemotherapy may help the immune system to increase a response against the tumor as well as to combat the tumor directly by the tumor cytotoxic modification of the RNA. This regimen could also control tumor growth.

The pharmaceutical composition or RNA formulation according to the invention may be used in combination with chloroquine, a pharmaceutical compound that impacts intracellular distribution (leakage from endosomes) and also increases cross presentation and thus the induction of antigen-specific effector T-cells.

The present RNA molecules are particularly suitable for use in inducing death of tumor and/or cancer cells and at the same time production, or increasing the level of, interferon-alpha (IFN-alpha). When added to human PBMC cells in vitro, the RNA composition at a final concentration of 5 micrograms per ml is capable of inducing production of at least 100 pg/ml IFN-alpha by 1 million human PBMCs cultivated 24 hours in 200 µl culture medium (typically RPMI plus 10% fetal calf serum).

A highly preferred pharmaceutical composition is an injectible formulation comprising the RNA of the invention in combination with a pharmaceutically acceptable excipient such as Ringer Lactate.

The present invention further provides a method of treating cancer and/or tumor in a subject, in particular by stimulating a host immune response and introducing an anti-metabolite into cancer/tumor cells in a subject, preferably a mammal, especially a human. An effective amount of a pharmaceutical composition according to the invention is administered, optionally in combination with another therapeutic treatment (for example, radiotherapy) or agent, such as a protein vaccine, an additional cancer chemotherapy agent, an additional immunomodulating agent, and/or a pharmaceutical drug modifying intracellular distribution and/or enhancing cross-priming such as chloroquine. Thus, the present invention also comprises the use of penetrating RNA formulation as defined herein for the preparation of a pharmaceutical composition or medicament for immunomodulation and cancer or tumor, respectively, therapy in a subject, preferably a mammal, especially a human.

Preferably, the additional immunomodulating agent is an anti-CTLA-4 or an anti PD1 or PDL1 or anti-regulatory T-cell reagent such as an anti-CD25 antibody or cyclophosphamide.

The at least one additional therapeutic agent may be administered simultaneously with the pharmaceutical composition of the invention, or the at least one additional therapeutic agent is administered sequentially with the pharmaceutical composition according to the present invention.

According to the method of the present invention it is preferred that IFN-alpha level is increased by the administration of the immunostimulating composition of the invention.

The method and composition of the present invention may be used to supplement IFN-alpha treatment, or to increase IFN-alpha in a subject. The method and composition of the present invention may be used to supplement interferon treatments, or to increase interferons (e.g. alpha, beta or lambda) in a subject, preferably a mammal, more preferred a human.

The pharmaceutical composition of the invention typically comprises, in addition to RNA in the dication-containing solution, and other therapeutic or immunogenic agents, a pharmaceutically acceptable carrier and/or a pharmaceutically acceptable vehicle and/or pharmaceutically acceptable diluent. Appropriate routes for suitable formulation and preparation of the RNA agents and compositions according to the invention and the are disclosed in Remington: "The Science and Practice of Pharmacy," 20th Edn., A. R. Gennaro, Editor, Mack Publishing Co., Easton, Pa. (2003). Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxypropylene copolymers. RNA compositions according to the invention can comprise filler substances or substances such as lactose, mannitol, substances for covalent linking of polymers (for example polyethylene glycol), or inclusion of materials in or on particular preparations of polymer compounds, such as e.g. polylactate, polyglycolic acid, hydrogel or to liposomes, microemulsions, micelles, unilamellar or multilamellar vesicles, erythrocyte fragments or spheroblasts. The particular embodiments of the RNA agent and compositions are chosen according to the physical and chemical properties, for example in respect of solubility, stability, bioavailability or degradability. Controlled or constant release of the active drug (-like) components according to the invention includes formulations based on lipophilic depots (e.g. fatty acids, waxes or oils). RNA formulations or compositions according to the invention can furthermore have protective coatings, e.g. protease inhibitors or permeability intensifiers. Preferred carriers are typically aqueous carrier materials, water for injection (WFI) or water buffered with phosphate, citrate, HEPES or acetate, or Ringer or Ringer Lactate etc. being used, and the pH is typically adjusted to 5.0 to 8.0, preferably 6.5 to 7.5. The carrier or the vehicle will additionally preferably comprise salt constituents, e.g. sodium chloride, potassium chloride or other components which render the solution e.g. isotonic. Furthermore, the carrier or the vehicle can contain, in addition to the abovementioned constituents, additional components, such as human serum albumin (HSA), polysorbate 80, sugars or amino acids.

The mode and method of administration and the dosage of the pharmaceutical compositions according to the invention depend on the nature of the disease to be treated and, where appropriate, the stage thereof, the antigen (in the case of using the present compositions together with a vaccine) and also the body weight, the age and the sex of the patient.

The pharmaceutical composition of the present invention may preferably be administered to the patient parenterally, e.g. intravenously, intraarterially, subcutaneously, intradermally, intra-lymph node or intramuscularly. It is also possible to administer the medicaments as defined herein topically or orally. According to preferred embodiments, the composition is administered by injection into a tumor tissue or tumor cavity, e.g. after a tumor is removed by surgery such as in the case of brain tumors.

Examples of cancers treatable with the immunostimulating composition, according to the invention include malignant melanoma, all types of carcinoma (colon, renal cell, bladder, prostate, non-small cell and small cell lung carcinoma, etc.), lymphomas, sarcomas, blastomas, gliomas, etc.

A further embodiment of the RNA molecule of the invention is a toxic coding RNA (mRNA in general with the following structure: 5' cap, coding sequence starting with a start codon and ending with a stop codon, untranslated 3' end followed by a poly-A tail) comprising the combined immunostimulatory activity and tumor cytotoxic chemical modification as outlined above. Preferably, the mRNA species contains a poly-G (more than three consecutive G residues) or a poly-U (more than four consecutive U residues) or a GPurine(n)G (where Purine is G or A residues and n from 1 to 4 or more) sequence(s) such that it can penetrate cells thereby allowing transient transgenic protein expression. Messenger RNA coding for a protein of interest can be produced in vitro by transcription using for example a plasmid DNA matrix. If needed, a poly-G (more than three consecutive G residues) or a poly-U (more than 4 consecutive U residues) or a GPurine(n)G (where Purine is G or A residues and n from 1 to 4 or more) sequence can for example be added after the poly-A tail by adding in the DNA matrix a poly-dG (more than three consecutive dG residues) or a poly-dT (more than 4 consecutive dT residues) or a dGdPurine(n)dG (where dPurine is dG or dA residues and n from 1 to 4 or more) sequence (d stands for deoxy). Alternatively, poly-G or poly-U sequences can be added to the mRNA using terminal transferase.

The invention claimed is:

1. A composition comprising:
an RNA molecule having an immunostimulating activity in a dication containing solution, wherein the RNA molecule has a chemical modification which is tumor cytotoxic chemical moiety being a cyanide group or a tumor toxin or an inhibitor of tyrosine kinase or an inhibitor of mutated oncogene.

2. The composition of claim 1 wherein the RNA molecule activates TLR-3 and/or TLR-7 and/or TLR-8 and/or RIG-I.

3. The composition of claim 1 wherein the chemical moiety linked to the RNA molecule is a tumor toxin and is selected from the group consisting of sunitinib, sorafenib and vemurafenib.

4. The composition according to claim 1 wherein the RNA molecule is an ssRNA oligonucleotide of 6 to 100 nucleotides.

5. The composition according to claim 1 wherein the RNA molecule comprises more than 100 nucleotides.

6. The composition according to claim 1 wherein the RNA molecule is present in complex with alkali metal ions.

7. The composition of claim 6 wherein the alkali metal ions are Na$^+$.

8. The composition according to claim 1 wherein the dication is Ca$^{2+}$.

9. The composition of claim 8 wherein the solution comprises Ringer lactate.

10. A composition comprising:
an RNA molecule having an immunostimulating activity in a dication containing solution, wherein the RNA molecule has a chemical modification which is toxic to tumor cells being one or more cytotoxic nucleotide analogue(s) having a chemical modification selected from the group consisting of 5-fluoro-uridine, 6-mercaptopurine, pentostatin and 2-chloro-adenine at a base and/or sugar moiety of the RNA molecule and the RNA molecule has one or more sequences selected from the group consisting of:

A5A55C55G5A5GGGGGG (SEQ ID NO: 1)

GGGGGGA55C55G5A5A5 (SEQ ID NO: 2)

AG5G55A5C55G5A5GGGGGG (SEQ ID NO: 3)

A5A55C55G5A5GGGGGGGGGGGG (SEQ ID NO: 4)

GGGGGGA5A55C55G5A5GGGGGG (SEQ ID NO: 5)

A5A55555G5A5GGGGGG (SEQ ID NO: 6)

GGGGGGA5A55C55G5A5GGGGGG (SEQ ID NO: 7)

wherein the above sequences are written, from left to right, in 5' to 3' direction, and "5" denotes a 5-fluoro-uridine nucleotide.

11. The composition of claim 10 wherein the RNA molecule is an ssRNA oligonucleotide of 6 to 100 nucleotides.

12. The composition of claim 10 wherein the RNA molecule comprises more than 100 nucleotides.

13. The composition of claim 10 wherein the RNA molecule is present in complex with alkali metal ions.

14. The composition of claim 13 wherein the alkali metal ions are Na$^+$.

15. The composition of claim 10 wherein the dication is Ca$^{2+}$.

16. The composition of claim 15 wherein the solution comprises Ringer lactate.

17. The composition of claim 10 wherein the RNA molecule activates TLR-3 and/or TLR-7 and/or TLR-8 and/or RIG-I.

18. The composition according to claim 10 wherein the RNA molecule further comprises additional chemically modified and/or labelled nucleotides.

19. A composition comprising:
an RNA molecule having an immunostimulating activity in a dication containing solution, wherein the RNA molecule has a chemical modification which is toxic to tumor cells being one or more cytotoxic nucleotide analogue(s) having a chemical modification selected from the group consisting of cytarabine, fludarabine and gemcitabine at a base and/or sugar moiety of the RNA molecule.

20. The composition of claim 19 wherein the RNA molecule is an ssRNA oligonucleotide of 6 to 100 nucleotides.

21. The composition of claim 19 wherein the RNA molecule comprises more than 100 nucleotides.

22. The composition of claim 19 wherein the RNA molecule is present in complex with alkali metal ions.

23. The composition of claim 22 wherein the alkali metal ions are $Na^+$.

24. The composition of claim 19 wherein the dication is $Ca^{2+}$.

25. The composition of claim 24 wherein the solution comprises Ringer lactate.

26. The composition of claim 19 wherein the RNA molecule activates TLR-3 and/or TLR-7 and/or TLR-8 and/or RIG-I.

* * * * *

SEQUENCE LISTING

```
<160> NUMBER OF SEQ ID NOS: 7

<210> SEQ ID NO 1
<211> LENGTH: 18
<212> TYPE: RNA
<213> ORGANISM: artificial sequences
<220> FEATURE:
<221> NAME/KEY: source
<222> LOCATION: 1..18
<223> OTHER INFORMATION: /mol_type="RNA"
      /note="Immunostimulating and tumor cytotoxic RNA"
      /organism="artificial sequences"
<220> FEATURE:
<221> NAME/KEY: mod_base=OTHER
<222> LOCATION: 2
<223> OTHER INFORMATION: /note="5-fluoro-uridine"
<220> FEATURE:
<221> NAME/KEY: mod_base=OTHER
<222> LOCATION: 4..5
<223> OTHER INFORMATION: /note="5-fluoro-uridine"
<220> FEATURE:
<221> NAME/KEY: mod_base=OTHER
<222> LOCATION: 7..8
<223> OTHER INFORMATION: /note="5-fluoro-uridine"
<220> FEATURE:
<221> NAME/KEY: mod_base=OTHER
<222> LOCATION: 10
<223> OTHER INFORMATION: /note="5-fluoro-uridine"
<220> FEATURE:
<221> NAME/KEY: mod_base=OTHER
<222> LOCATION: 12
<223> OTHER INFORMATION: /note="5-fluoro-uridine"

<400> SEQUENCE: 1
auauucuugu augggggg                                              18

<210> SEQ ID NO 2
<211> LENGTH: 18
<212> TYPE: RNA
<213> ORGANISM: artificial sequences
<220> FEATURE:
<221> NAME/KEY: source
<222> LOCATION: 1..18
<223> OTHER INFORMATION: /mol_type="RNA"
      /note="Immunostimulating and tumor cytotoxic RNA"
      /organism="artificial sequences"
<220> FEATURE:
<221> NAME/KEY: mod_base=OTHER
<222> LOCATION: 8..9
<223> OTHER INFORMATION: /note="5-fluoro-uridine"
<220> FEATURE:
<221> NAME/KEY: mod_base=OTHER
<222> LOCATION: 11..12
<223> OTHER INFORMATION: /note="5-fluoro-uridine"
<220> FEATURE:
<221> NAME/KEY: mod_base=OTHER
<222> LOCATION: 14
<223> OTHER INFORMATION: /note="5-fluoro-uridine"
<220> FEATURE:
<221> NAME/KEY: mod_base=OTHER
<222> LOCATION: 16
<223> OTHER INFORMATION: /note="5-fluoro-uridine"
<220> FEATURE:
<221> NAME/KEY: mod_base=OTHER
<222> LOCATION: 18
<223> OTHER INFORMATION: /note="5-fluoro-uridine"

<400> SEQUENCE: 2
```

```
gggggggauuc uuguauau                                              18
```

```
<210> SEQ ID NO 3
<211> LENGTH: 21
<212> TYPE: RNA
<213> ORGANISM: artificial sequences
<220> FEATURE:
<221> NAME/KEY: source
<222> LOCATION: 1..21
<223> OTHER INFORMATION: /mol_type="RNA"
      /note="Immunostimulating and tumor cytotoxic RNA"
      /organism="artificial sequences"
<220> FEATURE:
<221> NAME/KEY: mod_base=OTHER
<222> LOCATION: 3
<223> OTHER INFORMATION: /note="5-fluoro-uridine"
<220> FEATURE:
<221> NAME/KEY: mod_base=OTHER
<222> LOCATION: 5..6
<223> OTHER INFORMATION: /note="5-fluoro-uridine"
<220> FEATURE:
<221> NAME/KEY: mod_base=OTHER
<222> LOCATION: 8
<223> OTHER INFORMATION: /note="5-fluoro-uridine"
<220> FEATURE:
<221> NAME/KEY: mod_base=OTHER
<222> LOCATION: 10..11
<223> OTHER INFORMATION: /note="5-fluoro-uridine"
<220> FEATURE:
<221> NAME/KEY: mod_base=OTHER
<222> LOCATION: 13
<223> OTHER INFORMATION: /note="5-fluoro-uridine"
<220> FEATURE:
<221> NAME/KEY: mod_base=OTHER
<222> LOCATION: 15
<223> OTHER INFORMATION: /note="5-fluoro-uridine"

<400> SEQUENCE: 3
aguguuaucu uguauggggg g                                           21
```

```
<210> SEQ ID NO 4
<211> LENGTH: 24
<212> TYPE: RNA
<213> ORGANISM: artificial sequences
<220> FEATURE:
<221> NAME/KEY: source
<222> LOCATION: 1..24
<223> OTHER INFORMATION: /mol_type="RNA"
      /note="Immunostimulating and tumor cytotoxic RNA"
      /organism="artificial sequences"
<220> FEATURE:
<221> NAME/KEY: mod_base=OTHER
<222> LOCATION: 2
<223> OTHER INFORMATION: /note="5-fluoro-uridine"
<220> FEATURE:
<221> NAME/KEY: mod_base=OTHER
<222> LOCATION: 4..5
<223> OTHER INFORMATION: /note="5-fluoro-uridine"
<220> FEATURE:
<221> NAME/KEY: mod_base=OTHER
<222> LOCATION: 7..8
<223> OTHER INFORMATION: /note="5-fluoro-uridine"
<220> FEATURE:
<221> NAME/KEY: mod_base=OTHER
<222> LOCATION: 10
<223> OTHER INFORMATION: /note="5-fluoro-uridine"
<220> FEATURE:
<221> NAME/KEY: mod_base=OTHER
<222> LOCATION: 12
<223> OTHER INFORMATION: /note="5-fluoro-uridine"

<400> SEQUENCE: 4
auauucuugu augggggggg gggg                                        24
```

```
<210> SEQ ID NO 5
<211> LENGTH: 24
<212> TYPE: RNA
<213> ORGANISM: artificial sequences
<220> FEATURE:
<221> NAME/KEY: source
<222> LOCATION: 1..24
<223> OTHER INFORMATION: /mol_type="RNA"
      /note="Immunostimulating and tumor cytotoxic RNA"
      /organism="artificial sequences"
<220> FEATURE:
<221> NAME/KEY: mod_base=OTHER
<222> LOCATION: 8
<223> OTHER INFORMATION: /note="5-fluoro-uridine"
<220> FEATURE:
<221> NAME/KEY: mod_base=OTHER
<222> LOCATION: 10..11
<223> OTHER INFORMATION: /note="5-fluoro-uridine"
<220> FEATURE:
<221> NAME/KEY: mod_base=OTHER
<222> LOCATION: 13..14
<223> OTHER INFORMATION: /note="5-fluoro-uridine"
<220> FEATURE:
<221> NAME/KEY: mod_base=OTHER
<222> LOCATION: 16
<223> OTHER INFORMATION: /note="5-fluoro-uridine"
<220> FEATURE:
<221> NAME/KEY: mod_base=OTHER
<222> LOCATION: 18
<223> OTHER INFORMATION: /note="5-fluoro-uridine"

<400> SEQUENCE: 5 gggggauau ucuuguaugg gggg                                        24

<210> SEQ ID NO 6
<211> LENGTH: 18
<212> TYPE: RNA
<213> ORGANISM: artificial sequences
<220> FEATURE:
<221> NAME/KEY: source
<222> LOCATION: 1..18
<223> OTHER INFORMATION: /mol_type="RNA"
      /note="Immunostimulating and tumor cytotoxic RNA"
      /organism="artificial sequences"
<220> FEATURE:
<221> NAME/KEY: mod_base=OTHER
<222> LOCATION: 2
<223> OTHER INFORMATION: /note="5-fluoro-uridine"
<220> FEATURE:
<221> NAME/KEY: mod_base=OTHER
<222> LOCATION: 4..8
<223> OTHER INFORMATION: /note="5-fluoro-uridine"
<220> FEATURE:
<221> NAME/KEY: mod_base=OTHER
<222> LOCATION: 10
<223> OTHER INFORMATION: /note="5-fluoro-uridine"
<220> FEATURE:
<221> NAME/KEY: mod_base=OTHER
<222> LOCATION: 12
<223> OTHER INFORMATION: /note="5-fluoro-uridine"

<400> SEQUENCE: 6 auauuuugu augggggg                                               18

<210> SEQ ID NO 7
<211> LENGTH: 24
<212> TYPE: RNA
<213> ORGANISM: artificial sequences
<220> FEATURE:
<221> NAME/KEY: source
<222> LOCATION: 1..24
<223> OTHER INFORMATION: /mol_type="RNA"
      /note="Immunostimulating and tumor cytotoxic RNA"
      /organism="artificial sequences"
```

```
<220> FEATURE:
<221> NAME/KEY: mod_base=OTHER
<222> LOCATION: 8
<223> OTHER INFORMATION: /note="5-fluoro-uridine"
<220> FEATURE:
<221> NAME/KEY: mod_base=OTHER
<222> LOCATION: 10..11
<223> OTHER INFORMATION: /note="5-fluoro-uridine"
<220> FEATURE:
<221> NAME/KEY: mod_base=OTHER
<222> LOCATION: 13..14
<223> OTHER INFORMATION: /note="5-fluoro-uridine"
<220> FEATURE:
<221> NAME/KEY: mod_base=OTHER
<222> LOCATION: 16
<223> OTHER INFORMATION: /note="5-fluoro-uridine"
<220> FEATURE:
<221> NAME/KEY: mod_base=OTHER
<222> LOCATION: 18
<223> OTHER INFORMATION: /note="5-fluoro-uridine"

<400> SEQUENCE: 7 gggggggauau ucuuguaugg gggg                                    24
```